(12) United States Patent
Schmidt et al.

(10) Patent No.: US 8,588,557 B2
(45) Date of Patent: *Nov. 19, 2013

(54) INTEGRATED OPTICAL VAPOR CELL APPARATUS FOR PRECISION SPECTROSCOPY

(71) Applicants: The Regents of the University of California, Oakland, CA (US); Brigham Young University, Provo, UT (US)

(72) Inventors: Holger Schmidt, Capitola, CA (US); Aaron Roe Hawkins, Provo, UT (US)

(73) Assignees: The Regents of the University of California, Oakland, CA (US); Brigham Young University, Provo, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/754,173

(22) Filed: Jan. 30, 2013

(65) Prior Publication Data

US 2013/0199701 A1    Aug. 8, 2013

Related U.S. Application Data

(60) Continuation of application No. 13/161,748, filed on Jun. 16, 2011, now Pat. No. 8,385,693, which is a division of application No. 12/061,165, filed on Apr. 2, 2008, now Pat. No. 8,005,332.

(60) Provisional application No. 60/917,030, filed on May 9, 2007.

(51) Int. Cl.
*G02B 6/10* (2006.01)
*G01N 21/00* (2006.01)

(52) U.S. Cl.
USPC ............ 385/12; 385/131; 385/134; 356/432; 356/437; 356/440

(58) Field of Classification Search
USPC .......................................................... 385/12
See application file for complete search history.

(56) References Cited

U.S. PATENT DOCUMENTS

| | | | |
|---|---|---|---|
| 8,385,693 B2 * | 2/2013 | Schmidt et al. | 385/12 |
| 2004/0175837 A1 | 9/2004 | Bonne et al. | |
| 2004/0252957 A1 | 12/2004 | Schmidt et al. | |
| 2009/0045057 A1 * | 2/2009 | Hattori | 204/450 |

OTHER PUBLICATIONS

Alexandrov et al., "Light-Induced Desorption of Alkali-Metal Atoms From Paraffin Coating", Phys. Rev. A, Oct. 2002, 66, 042903-1-042903-12.

Barber et al., "Fabrication of Hollow Waveguides With Sacrificial Aluminum Cores", IEEE Phot. Tech. Letters, Feb. 2005, 17(2), 363-365.

(Continued)

*Primary Examiner* — Hemang Sanghavi
(74) *Attorney, Agent, or Firm* — Woodcock Washburn LLP

(57) ABSTRACT

An optical waveguide is provided comprising a non-solid core layer surrounded by a solid-state material, wherein light can be transmitted with low loss through the non-solid core layer. A vapor reservoir is in communication with the optical waveguide. One implementation of the invention employs a monolithically integrated vapor cell, e.g., an alkali vapor cell, using anti-resonant reflecting optical waveguides, or ARROW waveguides, on a substrate.

20 Claims, 6 Drawing Sheets
(6 of 6 Drawing Sheet(s) Filed in Color)

(56) References Cited

OTHER PUBLICATIONS

Benabid et al., "Compact, Stable and Efficient All-Fibre Gas Cells Using Hollow-Core Photonic Crystal Fibres", Nature, Mar. 2005, 434, 488-491.

Benabid et al., "Stokes Amplification Regimes in Quasi-cw Pumped Hydrogen-Filled Hollow-Core Photnic Crystal Fiber", Phys. Rev. Letters, Nov. 2005, 95, 2139903-1-2139903-4.

Briaudeau et al., "Sub-Doppler Spectroscopy in a Thin Film of Resonant Vapor", Phys. Rev. A, May 1999, 59(5), 3723-3735.

Couny et al., "Electromagnetically Induced Transparency and Saturable Absorption in All-Fiber Devices Based on $^{12}C_2H_2$-Filled Hollow-Core Photonic Crystal Fiber", Opt. Comm., Jan. 2006, 263, 28-31.

Danielli et al., "Frequency Stabilization of a Frequency-Doubled 1556-nm Source to the $5S_{e,fra\ 1/2}$-$5D_{e,fra\ 5/2}$ Two-Photon Transition of Rubidium", Opt. Letters, Jun. 2000, 25(12), 905-907.

Dawes et al., "All Optical Switching in Rubidium Vapor", Science, Apr. 2005, 308, 672-674.

Duguay et al., "Antiresonant Reflecting Optical Waveguides in $SiO_2$-Si Multilayer Structures", Appl. Phys. Letters, Jul. 1986, 49(1), 13-15.

Eisaman et al., "Electromagnetically Induced Transparency With Tunable Single-Photon Pulses", Nature, Dec. 2005, 438, 837-841.

Fink et al., "A Dielectric Omnidirectional Reflector", Science, Nov. 1998, 282, 1679-1682.

Ghosh et al., "Resonant Optical Interactions with Molecules Confined in Photonic Band-Gap Fibers", Phys. Rev. Letters, Mar. 2005, 94, 093902-1-093902-4.

Hadley et al., "Bragg Fiber Design for Linear Polarization", Opt. Letters, Apr. 2004, 29, 809-811.

Hansch et al., "Precision Spectroscopy of Hydrogen and Femtosecond Laser Frequency Combs", Phil. Trans. Royal Soc. London A., Aug. 2005, 363, 2155-2163.

Harris, "Electromagnetically Induced Transparency", Phys. Today, Jul. 1997, 50, 36-42.

Hau et al., "Light Speed Reduction to 17 Metres Per Second in an Ultracold Atomic Gas", Nature, Feb. 1999, 397, 594-598.

Knappe et al., "Atomic Vapor Cells for Chip-Scale Atomic Clocks with Improved Long-Term Frequency Stability", Opt. Letters, Sep. 2005, 30(18), 2351-2353.

Kolchin et al., "Generation of Narrow-Bandwidth Paired Photons: Use of a Single Driving Laser", Phys. Revl Letters, Sep. 2006, 97, 113602-1-113602-4.

Liew et al., "Microfabricated Alkali Atom Vapor Cells", Appl. Phys. Letters, Apr. 2004, 84(14), 2694-2696.

Lukin et al., "Controlling Photons Using Electromagnetically Induced Transparency", Nature, Sep. 2001, 413, 273-276.

Lukin, "*Colloquium*: Trapping and Manipulating Photon States in Atomic Ensembles", Rev. Mod. Phys., Apr. 2003, 75, 457-472.

Russell, "Holey Fiber Concept Spawns Optical-Fiber Renaissance", Laser Focus World, Sep. 2002, 38, 77-82.

Schmidt et al., "Electromagnetically Induced Transparency in Alkali Atoms Integrated on a Semiconductor Chip", Appl. Phys. Letters, Jan. 2005, 86, 032106-1-032106-3.

Schmidt et al., "Giant Kerr Nonlinearities Obtained by Electromagnetically Induced Transparency", Opt. Letters, Dec. 1996, 21(23), 1936-1938.

Schmidt et al., "Hollow-Core Waveguides and 2-D Waveguide Arrays for Integrated Optics of Gases and Liquids", IEEE J. of Selected Topics in Quantum Electronics, Mar./Apr. 2005, 11(2), 519-527.

Thapa et al., "Saturated Absorption Spectroscopy of Acetylene Gas Inside Large-Core Photonic Bandgap Fiber", Opt. Letters, Aug. 2006, 31(16), 2489-2491.

Xu et al., "Experimental Demonstration of Guiding and Confining Light in Nanometer-Size Low-Refractive-Index Material", Opt. Letters, Jul. 2004, 29(14), 1626-1628.

Yin et al., "Integrated Arrow Waveguides With Hollow Cores", Opt. Express, Jun. 2004, 12(12), 2710-2715.

Yin et al., "Single-Molecule Detection Sensitivity Using Planar Integrated Optics on a Chip", Opt. Letters, Jul. 2006, 31(14), 2136-2138.

\* cited by examiner

INTEGRATED OPTICAL VAPOR CELL APPARATUS FOR PRECISION SPECTROSCOPY

CROSS REFERENCE TO RELATED APPLICATIONS

This application is a continuation of U.S. patent application Ser. No. 13/161,748, filed Jun. 16, 2011, which is a divisional of U.S. patent application Ser. No. 12/061,165, filed Apr. 2, 2008, now U.S. Pat. No. 8,005,332, issued Aug. 23, 2011, which claims the benefit of U.S. Provisional Application No. 60/917,030, filed May 9, 2007, the entire contents of which are hereby incorporated by reference in their entireties.

GOVERNMENT RIGHTS

This invention was made by government support of Grant No. ECS-0500602 from The National Science Foundation and Grant No. FA9550-05-1-0432 from The Air Force Office of Scientific Research. The Government has certain rights in this invention.

TECHNICAL FIELD

The present invention relates generally to the field of integrated optics and saturation absorption atomic or molecular spectroscopy on a substrate, frequency references, or atomic clocks, utilizing an optical waveguide comprising a non-solid core layer surrounded by a solid-state material, wherein light can be transmitted with low loss through the non-solid core layer. A vapor reservoir is in communication with the optical waveguide. One implementation of the invention employs a monolithically integrated vapor cell, e.g., an alkali vapor cell, in vapor communication with anti-resonant reflecting optical waveguides, known as ARROWs or ARROW waveguides on a substrate.

BACKGROUND

Over the last few years, it has become possible to confine and guide light in micrometer-scale hollow-core waveguides based on photonic crystal structures like photonic crystal fiber (HC-PCF) (Russell, P., Laser Focus World 38: 77-82, 2002), omniguides (Fink, Y. et al. *Science* 282: 1679-1682, 1998), and Bragg waveguides (Hadley, et al., *Opt. Lett.* 29: 809-811, 2004). Benefits of this approach in the case of gas and vapor phase media include the miniaturization and simplification of existing measurement apparatuses, and—perhaps even more significant—the prospect of adding integrated optical components developed for all-solid photonics to implement new functionalities. Nonlinear optical devices are particularly attractive because the use of a waveguide eliminates the tradeoff between small beam areas and finite focal depth. This allows large intensities to be maintained over long distances. Consequently, there are numerous potential applications of hollow-core waveguide based atomic and molecular spectroscopy, including gas phase sensing, precision spectroscopy (Hansch, T W. et al., *Phil. Trans. Royal Soc. London A* 363: 2155-2163, 2005), atomic clocks (Knappe, S. et al. *Opt. Lett.* 30: 2351-2353, 2005), nonlinear frequency generation (Benabid, et al., *Phys. Rev. Lett.* 95, 213903, 2005), low-level all-optical switching (Dawes, et al., *Science* 308, 672-674, 2005), slow light (Lukin, MD. *Rev Mod Phys* 75:457-72, 2003; Hau, et al., *Nature* 397:594-598, 1999), and quantum communications (Eisaman MD. et al., *Nature,* 438: 837-841, 2005; Kolchin, et al., *Phys. Rev. Lett.* 97: 113602, 2006). The latter areas are examples of the use of electromagnetically induced transparency (EIT) (Harris, S E., *Phys. Today* 50: 36-42, 1997)—extremely strong linear and nonlinear light-matter interactions that result from quantum interference effects. Alkali metal vapors are ideally suited for EIT as well as for many other applications, making integrated rubidium or cesium cells highly desirable. Up to now, most work in the area of confined gas spectroscopy has been carried out with cylindrical photonic crystal (HC-PCF) fiber. Confinement and spectroscopy of gases (Benabid et al., *Nature* 434:488-491, 2005; Ghosh et al., *Phys. Rev. Lett.* 94: 093902, 2005), generation of nonlinear amplification (Benabid, et al., *Phys. Rev. Lett.* 95, 213903, 2005), EIT and saturated absorption spectroscopy in acetylene (Ghosh et al., *Phys. Rev. Lett.* 94: 093902, 2005; Couny et al., *Opt. Comm.* 263: 28-31, 2006; Thapa et al. *Opt. Lett.* 31: 2489-2491, 2006), and signatures of quantum interference in rubidium vapor (Ghosh et al., *Phys. Rev. Lett.* 97: 023603, 2006) have been demonstrated and are indicative of the promise and rapid progress in this field. The HC-PCF-based approach has many advantages, in particular low waveguide loss and resulting long interaction lengths. However, it also has limitations such as the current requirement for attaching rubidium reservoirs connected to a vacuum pump system at the open ends of the HC-PCF (Ghosh et al., *Phys. Rev. Lett.* 97: 023603, 2006) thereby preventing full integration and leaving the complete apparatus large. Another characteristic is the restriction of optical confinement and interaction to one dimension.

Guiding light through hollow optical waveguides has opened photonics to investigating non-solid materials with the convenience of integrated optics. Of particular interest is the confinement of atomic vapors such as alkali vapors, due to the wide range of applications including slow and stopped light (Lukin, MD, *Rev Mod Phys* 75:457-72, 2003), single-photon nonlinear optics (Schmidt, H. and Imanoglu, A., *Opt Lett* 21:1936-1938, 1996), quantum information processing (Eisaman MD et al., *Nature,* 438: 837-841, 2005), precision spectroscopy (Hansch, T. W. et al., *Phil. Trans. Royal Soc. London A* 363: 2155-2163, 2005), and frequency stabilization (Danielli, et al., *Opt. Lett.* 25: 905-907, 2000). A need exists in the art for an integrated platform to enable precision atomic or molecular spectroscopy that combines the advantages of photonic crystal-like structures with integrated optics.

SUMMARY

The present invention relates generally to the field of integrated optics and saturation absorption atomic or molecular spectroscopy on a substrate, frequency references, or atomic clocks, utilizing an optical waveguide and an optical measurement system. The optical waveguide can comprise a non-solid core layer surrounded by a solid-state material, wherein light and an atomic or molecular vapor can be confined and transmitted with low loss through the non-solid core layer. A vapor reservoir is in communication with the optical waveguide. One implementation of the invention employs a monolithically integrated vapor cell, e.g., an alkali vapor cell, using anti-resonant reflecting optical waveguides, ARROWs or ARROW waveguides, on a substrate.

An optical waveguide is provided which comprises a substrate made of a solid material and multiple layers of solid state material disposed on the substrate; a non-solid core extending through at least one of said multiple layers, whereby said non-solid core may be used to contain a sample material; a perpendicular waveguide portion for use in injecting light into said non-solid core; and a vapor reservoir for use in containing a vapor in communication with said non-solid core; wherein said multiple layers of solid state material are constructed to form anti-resonant reflecting layers adjacent to said non-solid core, whereby light is substantially prevented from leaking out of said core in a transverse direction. The vapor can be an alkali vapor, e.g., rubidium, cesium, or sodium, an elemental vapor, e.g., barium, or a molecular vapor, e.g., iodine, HCN, or acetylene. An optical measurement system or a planar atomic or molecular spectroscopy system are provided comprising the optical waveguide. A system for making parallel optical measurements is provided comprising an optical waveguide in one or more parallel channels within a solid state material.

An optical waveguide is provided which comprises a substrate made of a solid material and multiple layers of solid state material disposed on the substrate; a non-solid core extending through at least one of said multiple layers, whereby said non-solid core may be used to contain a vapor; an intersecting waveguide portion for use in injecting light into said non-solid core; and a vapor reservoir for use in containing the vapor in communication with said non-solid core; wherein said multiple layers of solid state material are constructed to form anti-resonant reflecting layers adjacent to said non-solid core, whereby light is substantially prevented from leaking out of said core in a transverse direction. The vapor can be an alkali vapor, e.g., rubidium, cesium, or sodium, an elemental vapor, e.g., barium, or a molecular vapor, e.g., iodine, HCN, or acetylene. The substrate can comprise Silicon (Si) and the multiple layers can comprise $SiO_2$ and SiN. In one aspect, the non-solid core has an index of refraction which is lower than the index of refraction of the surrounding solid-state material, and wherein light can be transmitted with low loss through the non-solid core. The intersecting waveguide portion can be configured to permit transmission of counterpropagating light in two or more directions through the channel to create narrow spectral features. The spectral features can result from transmission, absorption, or interference. The intersecting waveguide portion can be substantially perpendicular to said non-solid core. The intersecting waveguide portion can adjoin the channel at an angle between 0° and 180°. In one aspect, the intersecting waveguide portion can be substantially linear to said non-solid core. In a further aspect, the reservoir is sealed to said substrate by anodic bonding, epoxy, or solder, and the seal is an airtight seal. The reservoir can be sealed, for example, with an o-ring seal, a screw fitting, or by crimping at the end of the reservoir. The reservoir can be glass or metal, for example, copper. A vapor source can be in a form of solid, liquid or gas.

An optical waveguide generally structured as an anti-resonant reflecting optical waveguide (ARROW) is provided which comprises a substrate and multiple layers of solid state material, including $SiO_2$ and SiN, disposed on the substrate, and a non-solid core extending through at least one of said multiple layers, wherein said non-solid core has an index of refraction which is lower than the index of refraction of the surrounding solid-state material, and wherein light can be transmitted with low loss through the non-solid core; a multilayer reflector, e.g., a Fabry-Perot reflector or a Bragg reflector, adjacent to said non-solid core, for substantially preventing light from leaking out of said core in a transverse direction; an intersecting waveguide portion for use in injecting light into said non-solid core; a vapor reservoir for use in containing a vapor in communication with said non-solid core; and whereby said non-solid core may be used to contain said vapor whose optical properties are to be measured. Optical properties include, but are not limited to, light transmission, light absorption, interference, photon detection, or photon generation. In one aspect, the injected light is used for measuring absorption characteristics associated with said vapor. The intersecting waveguide can adjoin the channel at an angle between 0° and 180°. In one aspect, the intersecting waveguide portion can be substantially perpendicular to said non-solid core. The intersecting waveguide portion can be substantially linear to said non-solid core. The intersecting waveguide portion can be configured to permit transmission of counterpropagating light in two or more directions through the channel to create narrow spectral features. The spectral features can result from transmission, absorption, or interference.

An optical measurement system is provided which comprises an optical waveguide comprising a channel surrounded by a solid-state material, including a multilayer reflector, e.g., a Fabry-Perot reflector or a Bragg reflector, adjacent to said channel; a vapor reservoir for use in containing a vapor in communication with said non-solid core; and an intersecting waveguide portion for use in injecting light into the channel, wherein the intersecting waveguide portion is configured to permit transmission of counterpropagating light in two or more directions through the channel to create narrow spectral features. The spectral features can result from transmission, absorption, or interference. The intersecting waveguide can adjoin the channel at an angle between 0° and 180°. A structure for injecting light into said channel is provided wherein the injected light is guided within the channel and through said vapor, and a device for measuring selected optical properties associated with said vapor, wherein said selected optical properties include light transmission, light absorption, interference, photon detection, or photon generation associated with said vapor over macroscopic distances within the channel.

A system for making parallel optical measurements, comprising an optical waveguide comprising a generally planar solid-state material and one or more non-solid parallel channels within said solid-state material, including a multilayer reflector, e.g., a Fabry-Perot reflector or a Bragg reflector, adjacent to each channel, whereby light injected into said channels is substantially prevented from leaking out of said channels in a transverse direction; a vapor reservoir for use in containing a vapor in communication with said one or more parallel channels; and one or more intersecting waveguide portions for use in injecting light into the channels; and means for measuring selected optical properties associated with said vapor. The intersecting waveguide portion can be configured to permit transmission of counterpropagating light in two or more directions through the channel to create narrow spectral features. The spectral features can result from transmission, absorption, or interference. The system can be used for saturation absorption spectroscopy, frequency reference, or an atomic clock.

A planar atomic or molecular spectroscopy system is provided which comprises an optical waveguide comprising a channel surrounded by a solid-state material, including a multilayer reflector, e.g., a Fabry-Perot reflector or a Bragg reflector, adjacent to said channel, wherein said channel is configured for low loss at a first optical wavelength and high loss at a second optical wavelength; a vapor reservoir for use in containing a vapor in communication with said channel; and an intersecting waveguide portion for use in injecting light into the channel, wherein the intersecting waveguide portion is configured to permit transmission of counterpropagating light in two or more directions through the channel to create narrow spectral features. The spectral features can result from transmission, absorption, or interference. The system can be used for saturation absorption spectroscopy, frequency reference, or an atomic clock.

Other features and advantages of the present invention are described below.

BRIEF DESCRIPTION OF THE DRAWINGS

The file of this patent or application contains at least one drawing/photograph executed in color. Copies of this patent or patent application publication with color drawings will be provided by the Office upon request and payment of the necessary fee.

DETAILED DESCRIPTION OF ILLUSTRATIVE EMBODIMENTS

Figure 1:
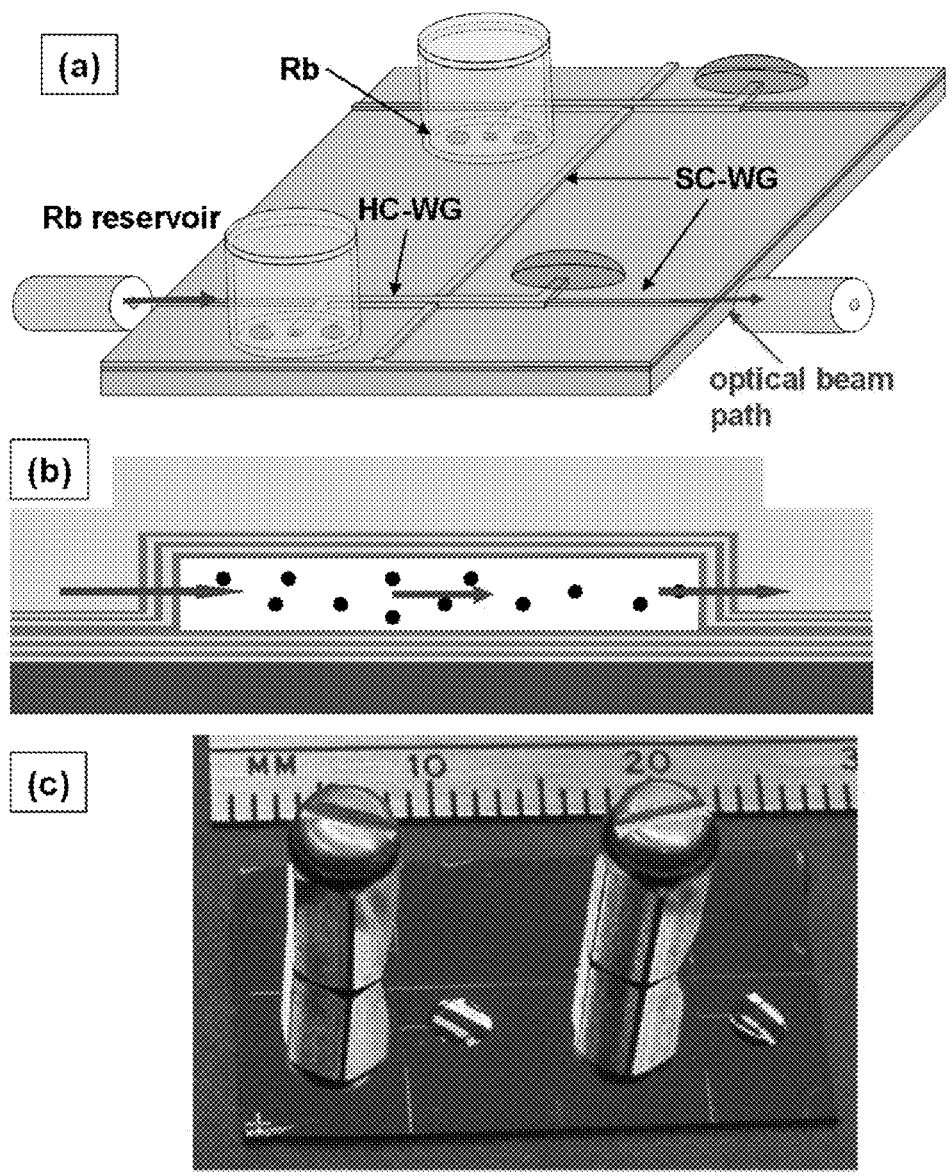
FIGS. 1(a)-1(c) show a planar atomic spectroscopy chip.

The present invention relates to an apparatus or system in integrated optics on a substrate which can be utilized in accurate measurements of atomic or molecular spectroscopy, for example, saturated absorption atomic spectroscopy. A system is provided which utilizes an optical waveguide comprising a non-solid core layer surrounded by a solid-state material, wherein light and atomic or molecular vapor can be transmitted with low loss through the non-solid core layer. A vapor reservoir is in communication with the non-solid core of the optical waveguide. One implementation of the invention employs a monolithically integrated atomic or molecular vapor cell, e.g., an alkali vapor cell, using anti-resonant reflecting optical waveguides, ARROWs or ARROW waveguides, on a substrate.

The present invention provides a monolithically integrated atomic or molecular vapor cell using hollow-core antiresonant reflecting optical waveguides (ARROWs) on a substrate. The cells have a footprint below 1 cm$^2$, fully planar fiber-optical access, and a cell volume more than seven orders of magnitude less than conventional bulk cells. The micron-sized mode areas enable high beam intensities over near-centimeter lengths. Optical densities have been demonstrated in excess of 2 and saturation absorption spectroscopy on a chip. These results enable the study of atoms and molecules on a platform that combines the advantages of photonic crystal-like structures with integrated optics.

In an embodiment of the invention, a monolithically integrated, planar rubidium vapor cell on a substrate is provided. We experimentally demonstrate the key requirements for integrated atomic spectroscopy, including confinement of both light and rubidium vapor in micron-scaled hollow-core optical waveguides, e.g., ARROW waveguides, large optical density over chip-scale distances, high intensities for efficient nonlinear effects, and fiber optics based saturation absorption spectroscopy. In addition, we demonstrate that the design of our atomic spectroscopy platform can contain functional features that cannot be implemented by using photonic crystal fibers.

This approach provides advantages compared to state-of-the-art techniques:

low-loss guiding of light inside a narrow channel of low-index media (gaseous or liquid) on a semiconductor chip. Low-index in this context means that the refractive index of the sample material is less than any of the indices of the solid-state host material.

Ability to guide light in the same volume as the low-index material. This allows for transmission, absorption or interference measurements over macroscopic distances.

Ability to discriminate/filter selective wavelengths along the sample volume. This results from the fact that the waveguide is optimized for a desired wavelength range.

Entirely planar technology for high sensitivity optical measurements compatible with fiber-optic technology.

Massive parallelism for multiple measurements on a single chip.

Potential for further integration with additional optical elements such as photo detectors on the same chip.

Ability for optical measurements on microchannels of an order of magnitude smaller dimension.

Specific methods to fabricate hollow-core ARROW waveguides based on sacrificial core layers.

Platform for realizing large nonlinear phase shifts between light signals using EIT in atoms, e.g., Rb.

Integrated platform for saturation spectroscopy and frequency stabilization.

Fiber-optic coupling.

Automatic alignment of counter-propagating beam by the optical waveguide for optimized interaction.

Can be integrated with other optical/electrical elements on a chip.

Possibility to add integrated temperature control or magnetic fields on the chip.

Possibility to achieve local control over temperature or magnetic fields via microstructuring of the underlying chip.

An atomic or molecular vapor cell in communication with an optical waveguide can be used for specific applications, for example, frequency stabilization or atomic or molecular references. The waveguide can be loaded either by atomic/molecular diffusion or by heating the chip, wherein the vapors or gases move into the non solid core of the waveguide.

An intersecting solid waveguide portion can inject light into the non-solid core waveguide. The intersection of the waveguides can be substantially perpendicular or substantially in the linear direction, or at various intermediate angles of intersection, for example, at an angle between 0° and 180°. A substantially linear intersection allows the automatic alignment of counterpropagating beams which is important for frequency stabilization as well as fiber optic coupling of light into the non-solid core waveguide.

Vapor reservoirs containing vapor sources such as rubidium are attached to the substrate by an air-tight seal. Reservoirs can be made from materials, including but not limited to, glass or metal. The reservoir can be attached to the chip through anodic bonding, epoxies, or solders to provide an air-tight seal between the substrate and the reservoir. The reservoirs can be placed over an opening at the end of the waveguide so that vapor contained in the reservoir can fill the hollow waveguide. Sources for the vapor include solids, for example, rubidium or cesium placed in the reservoir, liquids placed into the reservoir, or gases that were injected into the reservoir. After inserting a solid, liquid, or gas vapor source, the reservoir can be sealed using epoxy, a metal compression fitting, soldering, welding, anodic bonding, heating or crimping the end of the reservoir. Furthermore, an o-ring seal or a screw fitting can be used to seal the reservoir.

One goal of ours is to have highly functional, highly parallel structures naturally combined with other integrated elements such as interferometers and detectors on the same chip.

The research described herein provides a demonstration of waveguiding of light and/or atomic or molecular vapors in ARROW structures with gaseous or liquid core layers providing a wide range of applications including slow and stopped light, single-photon nonlinear optics, quantum information processing, precision spectroscopy, and frequency stabilization.

As a result of our research, better measurement tools will evolve that will improve both our fundamental understanding of health-related processes and physical measurement techniques as well as lead to improved flow cytometry methods.

Below we provide a more detailed description of exemplary embodiments and applications of the present invention. The focus can be on fluid applications, as well as applications to gases. In addition, it should be noted that invention may be carried out with a variety of substrate and waveguide materials, including the materials discussed in connection with the examples described below as well as those listed below (this list is not intended to be exhaustive).

Exemplary substrates are provided:
Semiconductors (useful for integrating electronic and optoelectronic devices (III-V semiconductors) with the waveguide), including silicon, Ge, diamond, all III-V semiconductors (GaAs, InP, HgCdTe, GaN, GaP, etc.).
Metals (useful for making a low cost device), including Al, Tin, Titanium, Copper, etc.
Plastics and Polymers (again useful for a low cost device and integrating with electronics on PCB boards). Insulators like ceramic or glass (useful because they produce a transparent substrate or because of heat mitigation).
Silicon based glasses—silica, quartz, soda lime, boron doped, etc.
alumina, sapphire
Exemplary waveguide materials:
Any material possibly deposited by chemical vapor deposition, including silicon dioxide, silicon nitride, silicon oxy-nitride (important because they are very commonly deposited by chemical vapor deposition).
Any material that could be sputtered or evaporated onto a substrate, including silicon dioxide, silicon nitride, and silicon-oxynitride.
Any material that could be spun-on or dip coated including spin-on-glass, polyimides, and polymer based materials.
Exemplary sacrificial layer materials:
Any metal, including aluminum, silver, gold, titanium, tungsten, copper.
Polymer materials, including SU8, photoresist, and polyimide.

DETAILED DESCRIPTION OF EXEMPLARY IMPLEMENTATIONS AND APPLICATIONS

We will now explain our invention in sufficient detail to enable a person of ordinary skill in the field of integrated optics to make and use the invention without undue experimentation. The following description is not intended (nor would it be possible) to serve as an exhaustive discussion of every possible embodiment, application or method of manufacturing a device within the scope of our invention. It is sufficient, however, to enable the skilled artisan to practice our invention. We will first briefly discuss our preliminary studies and then we will explain a method for fabricating exemplary embodiments of the invention, optical measurements for characterization and testing, an integrated rubidium cell and saturation absorption atomic spectroscopy utilizing an integrated ARROW rubidium vapor cell.

Nonlinear optical devices, such as ARROW waveguide atomic or molecular vapor cells, are particularly attractive because the use of a waveguide eliminates the tradeoff between small beam areas and finite focal depth. This allows large intensities to be maintained over long distances. Consequently, there are numerous potential applications of hollow-core waveguide based atomic and molecular spectroscopy, including gas phase sensing, precision spectroscopy (Hänsch, T W. et al., *Phil. Trans. Royal Soc. London A* 363: 2155-2163, 2005), atomic clocks (Knappe, S. et al., *Opt. Lett.* 30: 2351-2353, 2005), nonlinear frequency generation (Benabid, et al., *Phys. Rev. Lett.* 95, 213903, 2005), low-level all-optical switching (Dawes, et al., *Science* 308, 672-674, 20050, slow light (Lukin, MD, *Rev Mod Phys* 75:457-72, 2003; Hau, et al., *Nature* 397:594-598, 1999), and quantum communications (Eisaman MD, et al., *Nature*, 438: 837-841, 2005; Kolchin, et al., *Phys. Rev. Lett.* 97: 113602, 2006). The latter areas are examples of the use of electromagnetically induced transparency (EIT) (Harris, S. E., *Phys. Today* 50: 36-42, 1997)—extremely strong linear and nonlinear light-matter interactions that result from quantum interference effects. Alkali metal vapors are ideally suited for EIT as well as for many other applications, making integrated rubidium or cesium cells highly desirable.

In an embodiment of the invention, a monolithically integrated rubidium vapor cell is provided using hollow-core antiresonant reflecting optical waveguides (ARROWs) on a silicon chip. The cells have a footprint below 1 cm$^2$, fully planar fiber-optical access, and a cell volume more than seven orders of magnitude less than conventional bulk cells. The micron-sized mode areas enable high beam intensities over near-centimeter lengths. We demonstrate optical densities in excess of 2 and saturation absorption spectroscopy on a chip. These results enable the study of atoms and molecules on a platform that combines the advantages of photonic crystal-like structures with integrated optics.

FIG. 1(a) shows a schematic overview of the planar integrated atomic spectroscopy chip (rubidium cell). Optical signals are guided on the chip using both hollow and solid core antiresonant reflecting optical waveguides (ARROWs). ARROWs are akin to photonic crystal or Bragg structures in that they rely on the use of dielectric layers with appropriate thicknesses for confinement of light (Duguay, et al., *Appl. Phys. Lett.* 49: 13-15, 1986). They do not, however, have to be based on periodic structures which result in a waveguide description based on photonic bands and Bragg wave vectors. It has been shown recently that quasi single mode hollow core waveguides for both air and liquids can be built on a chip using the ARROW principle which requires fulfilling the antiresonance condition for the transverse wave vector component in each dielectric layer (Yin, et al., *Opt. Express*, 12: 2710-2715, 2004). It is important to note that with proper layer design the hollow-core waveguides can be interfaced with solid core ARROWs as shown in the longitudinal cross section in FIG. 1B. These connections allow for simultaneous efficient light guiding along the hollow core and transmission between solid and hollow waveguides (Schmidt et al., *IEEE J. of Selected Topics in Quantum Electronics*, 11: 519-527, 2005) and has been used to demonstrate single molecule detection sensitivity in liquid cores (Yin et al., *Opt. Lett.* 31, 2136-2138, 2006). This capability is reflected by the design in FIG. 1(a) and is essential for creating self-contained optical volumes with sealed connections to the edges of a chip. It also enables two-dimensional waveguide networks which cannot easily be created with photonic crystal fibers. FIG. 1(a) also depicts how the vapor of interest is introduced into the waveguides. The hollow-core ARROWs have two open ends.

A reservoir containing solid rubidium is placed over one end, and the other end is sealed. The optical beam path is then filled with rubidium atoms due to rubidium's high vapor pressure. The cell is completely self-contained and no vacuum apparatus is required to interface the reservoirs. Moreover, the reservoirs are placed in a location where they do not interfere with the optical beam path. FIG. 1c is a photograph of an ARROW-chip that was fabricated using this method. The figure shows two Rb reservoirs in parallel on the same chip, illustrating one advantage of the planar integrated approach—realization of several independent cells on a single device in a small volume.

Figure 5:
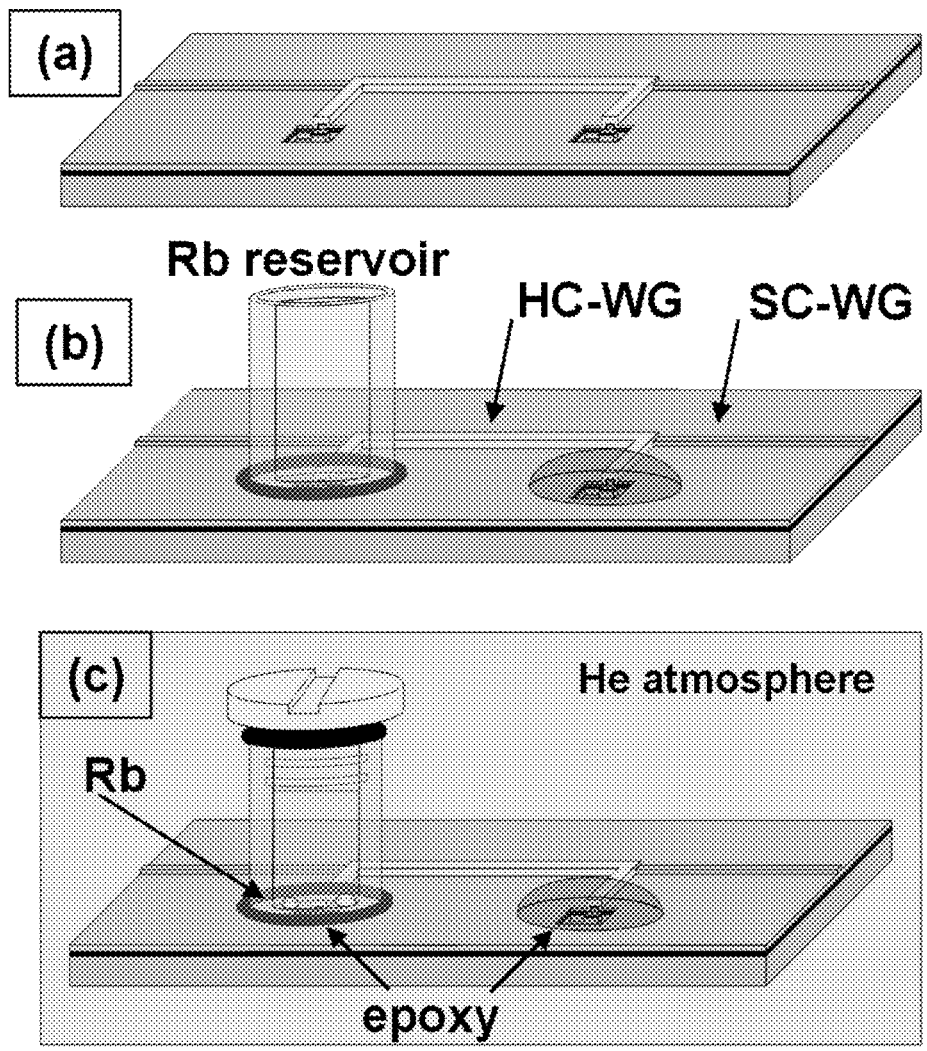
FIGS. 5(a)-5(c) show fabrication of an integrated rubidium cell.

The waveguide structures shown in FIG. 1(a)-(c) are formed using a previously described fabrication process (Barber J P. et al. *IEEE Phot. Tech. Lett.* 17: 363-365, 2005). The confinement layers are composed of plasma-enhanced chemical vapor deposited silicon nitride and oxide, and the hollow core is created by a sacrificial etching process (see Methods section for details). The reservoirs are attached and filled with natural rubidium in an inert helium atmosphere. Sealing to the chip is provided by epoxy adhesive and a metal screw on top of the reservoir (see FIG. 5 for details). It is important to note that the reservoirs are not part of the optical beam path and do not impact the optical properties of the ARROW-based cell. The waveguides were designed for low loss across the Rb D-lines (780 to 795 nm) in solid and hollow cores and transmissive connections between them using the design principles described in ref. 22.

FIG. 1(a)-(c) shows a planar atomic spectroscopy chip. a. Layout showing interconnected hollow-core (HC) and solid-core (SC) ARROW waveguides to form two independent vapor cells on a chip connected by additional SC waveguide. Sealed, rubidium-filled reservoirs are attached at the open ends of the HC waveguides. Fiber-optical access and beam path across the chip are shown for the lower vapor cell. b. Cross section along the HC-WG length showing the ARROW confinement layers (light grey: $SiO_2$, dark grey: SiN), beam path, and rubidium atoms inside HC-ARROW. c. Fabricated ARROW-based atomic spectroscopy chip (layout as in FIG. 1(a) but rotated clockwise by 90°). The optical beam path (red arrow) in the hollow core is 5 mm.

Figure 2:
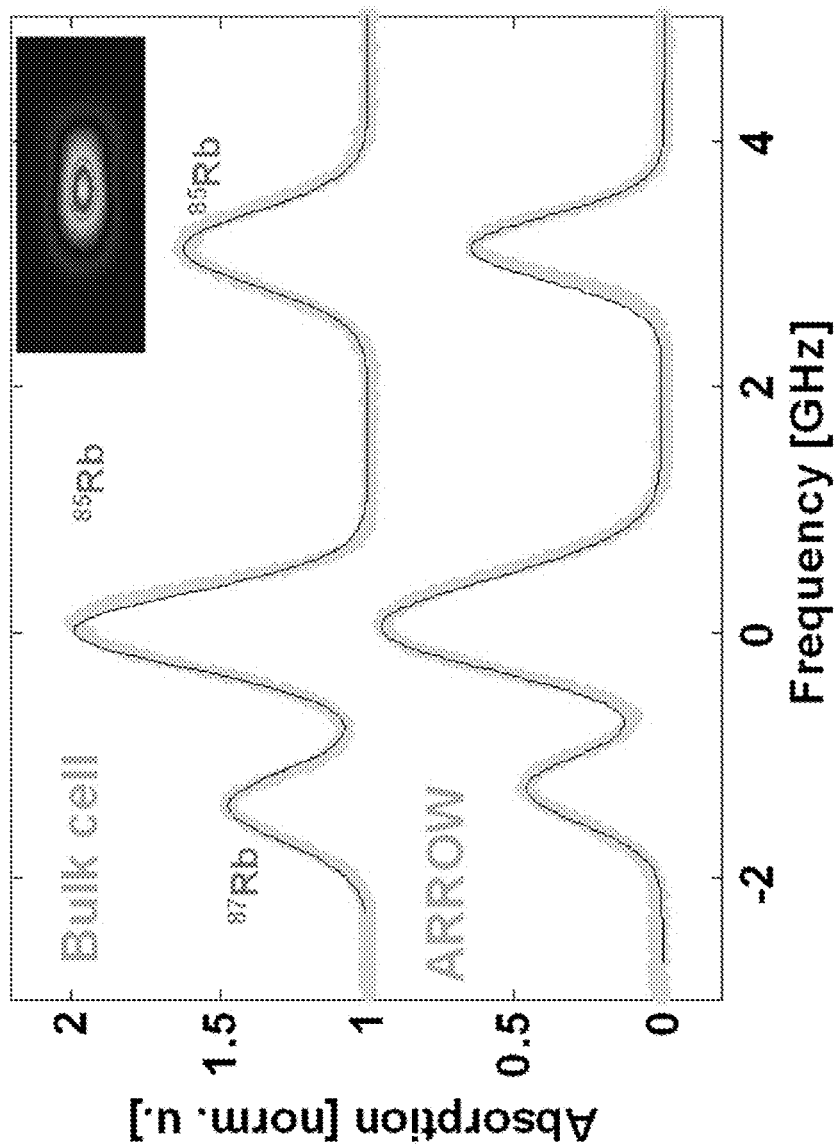
FIG. 2 shows rubidium spectroscopy on a chip.

For the following optical experiments, the chips were mounted on a waveguide translation stage. Light from tunable external cavity diode lasers was coupled into the solid-core ARROW as shown in FIG. 1(a) using end-coupling from a single-mode fiber. Transmitted light was collected with an objective lens, focused on a photodetector, and recorded as a function of wavelength (see Methods section and FIG. 6 for details). Alternatively, the excitation beam could be directed to a conventional bulk rubidium reference cell. FIG. 2 shows the normalized hyperfine-split absorption spectra of the Rb D2-line around 780 nm taken at a temperature of 70° C. for both bulk and integrated ARROW rubidium cells. Clearly, the integrated Rb cell shows a clean absorption signal that is nearly identical to that of the bulk cell, demonstrating the essential functionalities of the ARROW chip: confinement of both rubidium atoms and light within the same hollow-core waveguide. The black lines represent Gaussian fits to the spectra and are nearly indistinguishable from the data for both bulk and ARROW cell. A detailed analysis of the absorption spectrum and the broadening mechanisms will be presented elsewhere. Also shown in the figure is a mode image of the hollow-core mode taken on a sample with open hollow ends but identical core dimensions of 5×12 microns. The FWHM mode area in the hollow core is only $14\lambda^2 = 8.8\,\mu m^2$, showing that it is possible to confine light to areas comparable to atomic cross sections over macroscopic distances on a chip.

For comparison, the focal depth of a Gaussian beam of the same area would only be 22 µm, or a factor 230 shorter than the 5 mm propagation distance in the ARROW cell. As discussed in the introduction, the tight confinement over orders of magnitude longer lengths is particularly beneficial for nonlinear optical effects.

FIG. 2 shows rubidium spectroscopy on a chip. Normalized hyperfine absorption spectrum of natural rubidium D2 line for bulk (top) and integrated ARROW cell (bottom) at 70° C. The leftmost peak arises from $^{87}$Rb ($5S_{1/2}(F=2) \rightarrow 5P_{3/2}$), the other peaks from $^{85}$Rb ($5S_{1/2}(F=2) \rightarrow\!\!\!> 5P_{3/2}$), and $5S_{1/2}(F=3) \rightarrow 5P_{3/2}$). Each peak contains contributions from three transitions that are not resolved due to Doppler broadening. Black lines: Fits with Gaussian absorption profiles. Inset: ARROW waveguide mode image recorded with CCD camera.

Figure 3:
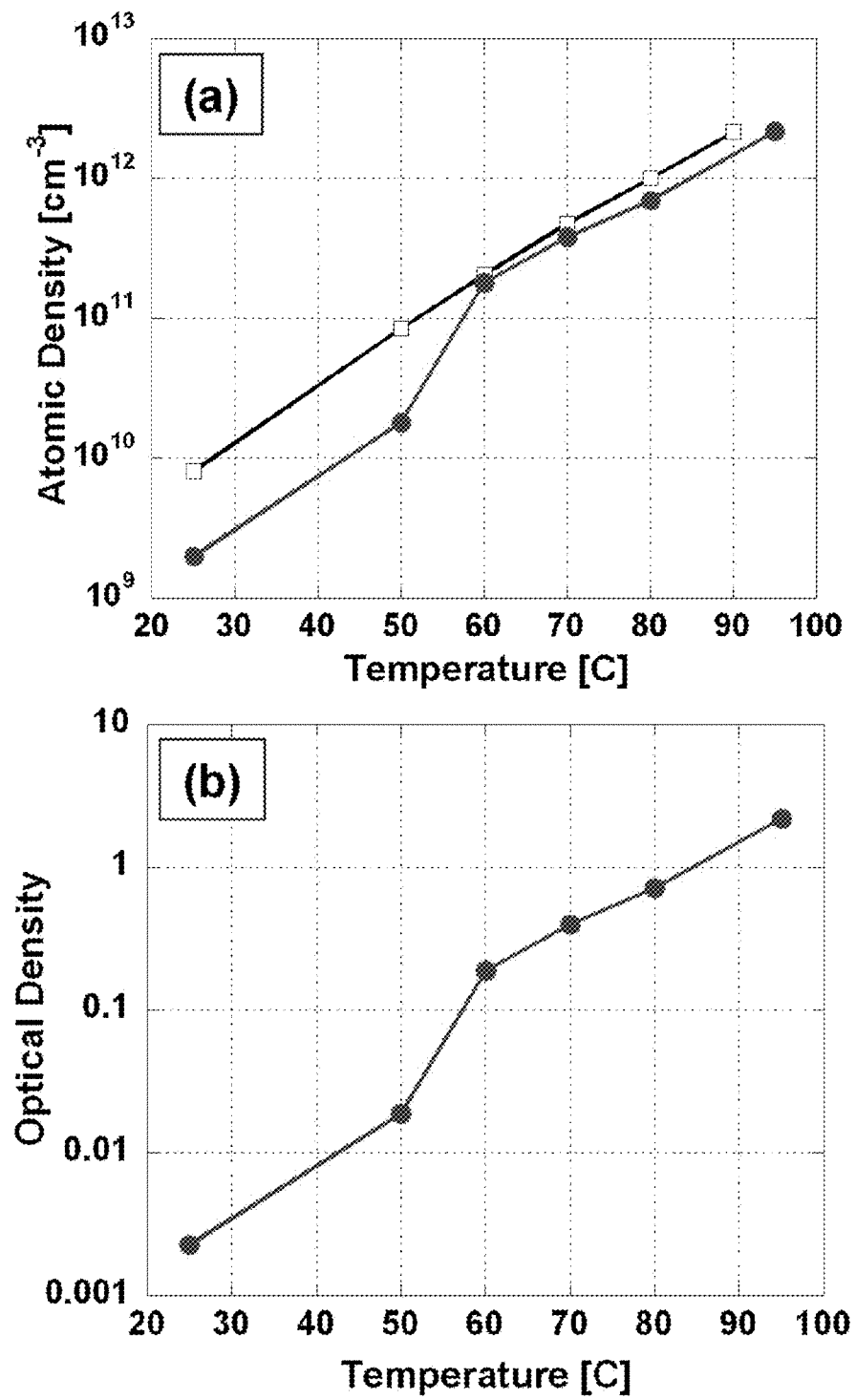
FIGS. 3(a)-(b) show characteristics of an integrated rubidium cell.

A key metric for the usefulness of an integrated rubidium cell, in addition to the ability to observe a guided mode and an absorption spectrum, are the levels of both atomic and optical density that can be achieved. In particular, it has been shown that EIT-based nonlinear effects require optical densities in excess of one to be truly practical (Lukin, M D. and Imamoglu, A, *Nature* 413: 273-276, 2001). In FIG. 3(a), we show the atomic densities that were extracted from the measured absorption profiles for both bulk and ARROW cells as a function of temperature. We find that density levels are similar in both cases although the integrated cell has larger deviations at lower temperatures where the optical signal from the ARROW cell is relatively noisy. The low temperature discrepancies likely stem from measurement uncertainties and atomic adhesion to the ARROW walls. FIG. 3B shows the corresponding optical density in the ARROW cell obtained from the $^{87}$Rb ($5S_{1/2}(F=1) \rightarrow\!\!\!> 5P_{3/2}$) absorption peak. We find that for temperatures above 85° C., an optically dense medium can be created for this weakest D2 transition, indicating that above this temperature the vapor is optically thick across the entire line. A maximum value of 2.21 at 95° C. is observed for this peak which demonstrates that the integrated ARROW cell is a promising candidate for nonlinear quantum coherence effects on a chip. Higher optical densities can be achieved with longer hollow-core sections and by increasing the atomic density, e.g. using light induced desorption (Alexandrov et al., *Phys. Rev. A* 66: 042903, 2002).

FIG. 3(a)-3(b) shows characteristics of integrated rubidium cell. a. Atomic density versus temperature for bulk (open squares) and integrated ARROW cell (circles). b. Optical density in integrated ARROW cell versus temperature for the weakest $^{87}$Rb ($5S_{1/2}(F=1) \rightarrow\!\!\!> 5P_{3/2}$) transition. An optically dense vapor (OD=α·L>1) is observed above 85° C.

Figure 4:
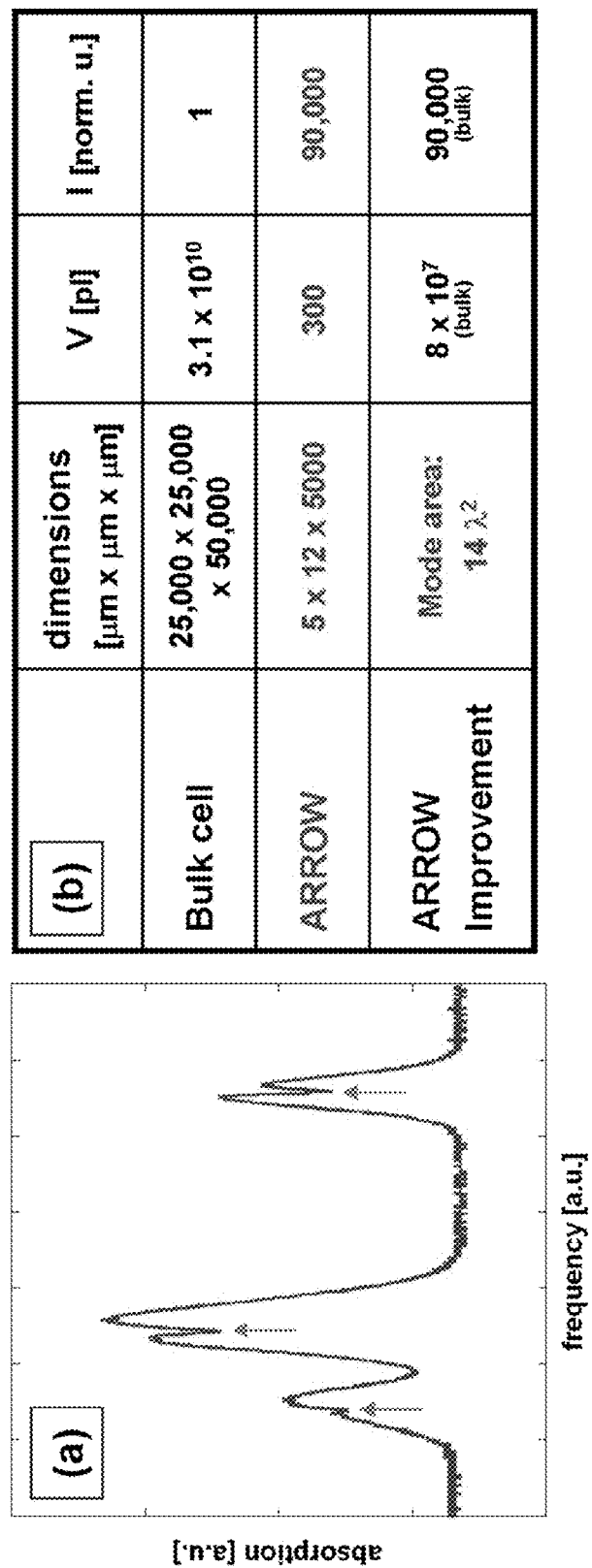
FIGS. 4(a)-4(b) show atomic spectroscopy on a chip and characteristics of an integrated ARROW Rb cell.

Finally, we investigated the suitability of the ARROW cell for common precision spectroscopy applications. The measurement setup was modified to accommodate coupling light from both ends into the chip to demonstrate saturated absorption spectroscopy (SAS) as detailed in the Methods section and FIG. 6. SAS is a commonly used method for frequency stabilization of a light source by locking its emission frequency to that of an atomic transition (Danielli et al., *Opt. Lett.* 25: 905-907, 2000). Typically, counterpropagating beams in bulk atomic vapor cells are used to create narrow spectral features by the elimination of Doppler broadening due to selection of atoms with zero velocity relative to the beams. The width of these Lamb dips is determined by the much smaller homogeneous linewidth of the transition and leads to more accurate references. Normally, overlapping the strong pump with the weaker probe beam requires some alignment effort. In our integrated ARROW cell, however, this alignment is automatically accomplished by the optical waveguides, demonstrating another advantage of the use of integrated optical elements. FIG. 4(a)-4(b) shows the SAS spectrum observed in the ARROW cell and clearly shows the characteristic Lamb dips. A width of approximately 34±2 MHz is observed which is consistent with additional homogeneous transit-time broadening.

We have presented a new type of integrated optical platform for atomic spectroscopy on a chip based on ARROW waveguides and demonstrated the essential functionalities as required for various applications, in particular nonlinear optics. The table in FIG. 4B summarizes the main properties of the ARROW-based rubidium cell in comparison with conventional bulk cells. The improvements afforded by the ARROW in terms of intensities and volume, range from over four to over seven orders of magnitude. We also compare its characteristics to cesium minicells that have recently been developed at NIST (Liew et al., *Appl. Phys. Lett.* 84: 2694-2696, 2004; Knappe, S. et al. *Opt. Lett.* 30: 2351-2353, 2005). While both are compact and excellent candidates for miniaturized atomic clocks, the optical ARROW cell volume and mode areas are orders of magnitude smaller and allows for much higher intensities, mainly due to the novel ability to guide light through the atomic medium on a chip. The integrated ARROW cells can be interfaced with conventional fiber and have immediate near-term applications, for example portable reference cells for frequency stabilization as demonstrated by the SAS experiment. Compared with HC-PCF fiber rubidium cells, the longer interaction path in a HC-PCF offers advantages for increasing the delay time in slow light experiments and for spectroscopy of molecular gases such as acetylene. For many applications, however, path lengths on the order of centimeters as in the ARROW cell are sufficient. For example, the large oscillator strengths of atoms means that only chip-scale distances are required to achieve high optical densities as demonstrated in FIG. 3B. Another example where short path lengths are beneficial is implementation of nonlinear optical effects such as giant Kerr nonlinearities (Schmidt, H. & Hawkins, A. R., *Appl. Phys. Lett.* 86: 032106, 2005) that are dispersion rather than absorption limited. In addition to the advantages illustrated in FIG. 1(c) (more compact total size and the straightforward definition of multiple cells on a single chip), additional unique possibilities in the ARROW cell arise from the option to add waveguides (See FIG. 1) that intersect the width of the cell. This could, for instance, be used to carry out sub-Doppler spectroscopy in thin vapor films (Briaudeau et al., *Phys. Rev. A* 59: 3723-3735, 1999) on a chip. The application of these cells to implementing quantum interference effects such as slow light or single photon nonlinearities on a chip presents a very intriguing and exciting path. In order to be able to fully utilize the quantum coherence phenomena, dephasing of the coherence between atomic levels must be avoided. This is challenging in tightly confined cells, but it was shown both theoretically (Schmidt, H. & Hawkins, A. R., *Appl. Phys. Lett.* 86: 032106, 2005) and experimentally in photonic crystal fibers (Ghosh et al., *Phys. Rev. Lett.* 97: 023603, 2006) that the dephasing can be sufficiently compensated by suitable organic wall coatings. The intersecting waveguide geometry is perfectly suited for quantum coherence based nonlinear single photon generation as it allows the collection and detection of photons generated in a degenerate parametric process by the solid core waveguides (Kolchin, et al., *Phys. Rev. Lett.* 97: 113602, 2006). In preliminary experiments, we have already observed Rb absorption in the ARROW cell after scattered light was coupled into the Rb cell via an intersecting solid core waveguide. In addition, different gases, functional waveguide geometries, and optical elements such as DBR gratings can be used on the ARROW platform, and some of the techniques described here may even be applied to nanophotonic structures such as slot waveguides (Xu et al., *Opt. Lett.* 29:1626-1628, 2004). All these options will stimulate further developments and new applications for atomic spectroscopy on a chip.

FIG. 4(a)-4(b) shows atomic spectroscopy on a chip and characteristics of integrated ARROW Rb cell. a. Saturation absorption spectroscopy (SAS) using counterpropagating beams in integrated ARROW cell. The grey arrows mark the Lamb dips resulting from the elimination of Doppler broadening. b. Comparison of main characteristics of integrated ARROW cell with conventional bulk vapor cell.

FIGS. 5(a)-5(c) shows fabrication of integrated rubidium cell. a. Chip after waveguide fabrication and opening ends of hollow core. b. Attachment of Rb reservoir (left) and epoxy seal (right) over open hollow-core waveguide ends. c. Addition of rubidium and sealing of reservoir in helium atmosphere.

Methods

Atomic Spectroscopy Chip Fabrication.

Hollow-core waveguides were built with a previously described process (Barber J P. et al. *IEEE Phot. Tech. Lett.* 17: 363-365, 2005) combining plasma-enhanced deposition of dielectric layers ($SiO_2$ and SiN) and patterning of a sacrificial core layer (SU-8; Microchem, Newton, Mass.). Solid-core waveguides for excitation and collection were formed by a photolithography step to define the solid-core ridge with a 1 μm deep reactive ion etch (Anelva Corp., Japan) in a $CF_4$ atmosphere. The ends of the SU-8 core were exposed using the same reactive ion etcher to locally remove the $SiO_2$ and SiN coating layers. The SU-8 core was then removed in a selective chemical etch (Nanostrip; Rockwood Electronic Materials, Fremont, Calif.). (FIG. 5(a)). FIG. 5(b) shows that after cleaving the chip to the desired size, a stainless steel standoff was attached over one of the open ends with an epoxy adhesive. The other open end was sealed with a drop of epoxy. The chip was then placed in a controlled environment glovebox (Vacuum Atmospheres, Hawthorne, Calif.) filled with helium. Solid rubidium droplets were then transferred from a glass ampoule source into the stainless steel standoff The top of the standoff was sealed using a stainless steel screw and butyl rubber o-ring as shown in FIG. 5(c), resulting in an integrated rubidium cell with helium buffer gas at atmospheric pressure.

The hollow core dimensions of the waveguide were 5×12 μm, and the solid core waveguide width was 12 μm. The dielectric layer sequence for the ARROW waveguides was starting from the substrate (all values in nm): $SiO_2$/SiN/$SiO_2$/SiN/$SiO_2$/SiN—core—SiN/$SiO_2$/SiN/$SiO_2$/SiN/$SiO_2$ (550/110/550/110/550/110/5000/303/216/162/379/139/3402).

Figure 6:
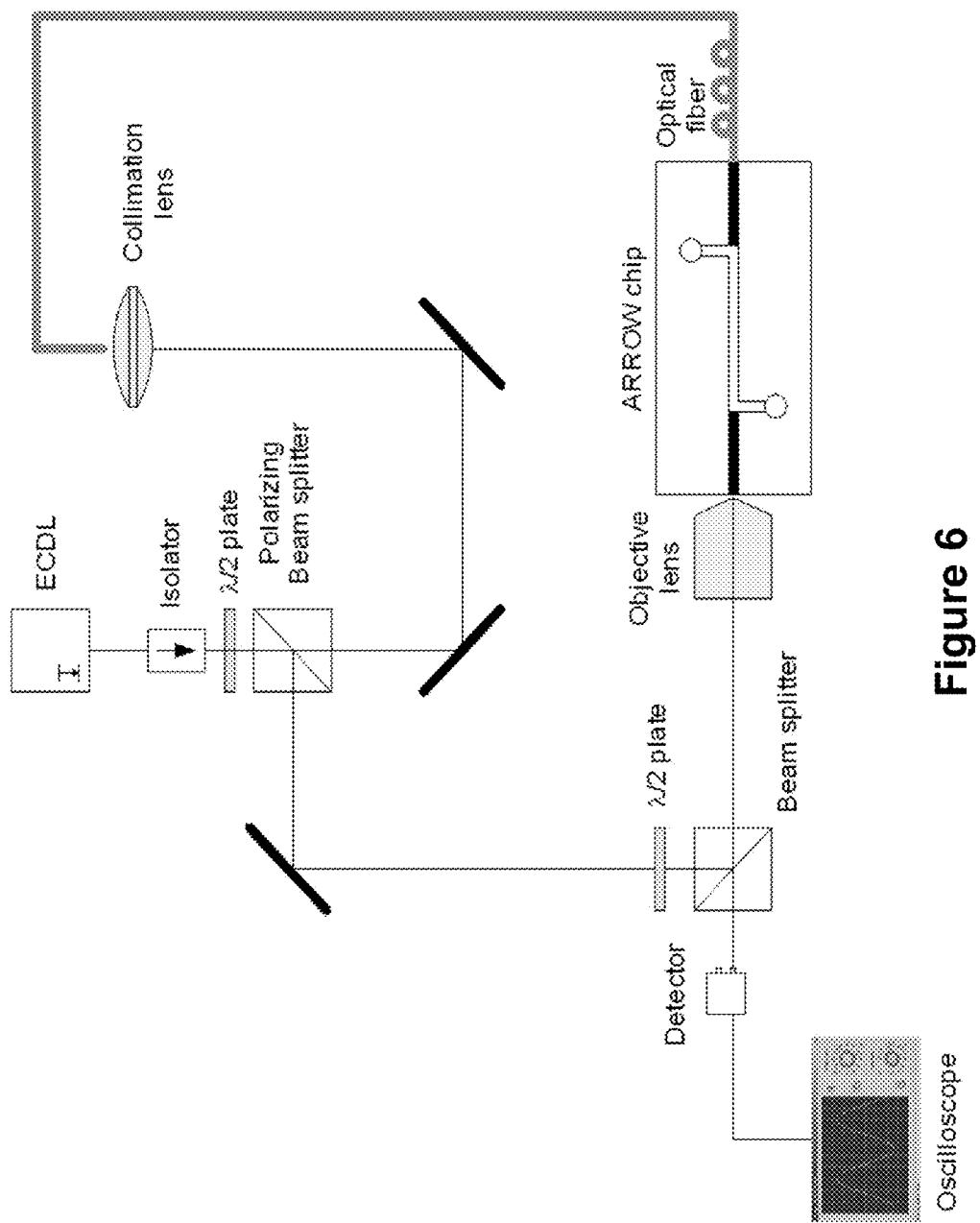
FIG. 6 shows a rubidium spectroscopy setup.

Saturated absorption spectroscopy (SAS). The setup for the SAS experiment is shown in FIG. 6. Light from a commercial external cavity diode laser (ECDL, New Focus) is first split by a polarizing beam splitter (PBS) into pump and probe beams. The probe is coupled into the waveguide via single mode optical fiber. The output from the probe beam is collected by an objective lens and monitored by a CCD camera. Once a good mode from the core area of the output facet is observed, the relative positions of objective lens and the waveguide are fixed, ensuring proper alignment of the counterpropagating pump beam. The pump beam is directed through a polarization independent beam splitter before it is coupled into the waveguide. The polarization direction of the probe and coupling beam can be controlled by the fiber polarization controller and the half-wave plate before the beam splitter, respectively. The relative power ratio of the probe and coupling beam is controlled by the half-wave plate before the first PBS. After both beams are coupled into the waveguide, the CCD camera is replaced by a photodetector to record the probe spectrum.

What is claimed:

1. A method for sealing a vapor reservoir to an integrated waveguide chip, the method comprising:
   attaching a first end of the vapor reservoir to the chip;
   placing an amount of vapor source inside the vapor reservoir;
   establishing a vacuum environment within the vapor reservoir; and
   sealing a second end of the vapor reservoir.

2. The method of claim 1, wherein the vapor reservoir has a metallic structure.

3. The method of claim 1, wherein the vapor reservoir is a copper cylinder.

4. The method of claim 1, wherein the vapor reservoir is made of glass.

5. The method of claim 1, wherein said attaching a first end of the vapor reservoir comprises placing the first end of the vapor reservoir over an opening at a first end of a waveguide comprised in the chip.

6. The method of claim 5 further comprising using epoxy to seal an opening at a second end of the waveguide.

7. The method of claim 1, wherein said attaching a first end of the vapor reservoir comprises creating an airtight seal between the first end of the vapor reservoir and the chip.

8. The method of claim 7, wherein said creating an airtight seal comprises using at least one member of a group consisting of anodic bond, epoxy, solder, metal compression fit, weld, heat, and crimp.

9. The method of claim 1, wherein the vapor source comprises using at least one member of a group consisting of alkali vapor, elemental vapor, and molecular vapor.

10. The method of claim 9, wherein the alkali vapor arises from an alkali metal element.

11. The method of claim 9, wherein the alkali vapor arises from one member of a group consisting of rubidium, cesium, and sodium.

12. The method of claim 9, wherein the elemental vapor comprises an alkaline earth metal element.

13. The method of claim 9, wherein the elemental vapor comprises barium.

14. The method of claim 9, wherein the molecular vapor comprises one member of a group consisting of iodine, acetylene, and hydrogen cyanide.

15. The method of claim 1, wherein the vapor source comprises one member of a group consisting of solid, liquid, and gas source.

16. The method of claim 1, wherein said steps of placing an amount of vapor source, establishing a vacuum environment, and sealing a second end of the vapor reservoir are conducted in a controlled environment glovebox.

17. The method of claim 1, wherein said establishing a vacuum environment comprises filling the vapor reservoir with an inert gas at atmospheric pressure.

18. The method of claim 17, wherein the inert gas is helium or nitrogen.

19. The method of claim 1, wherein said sealing a second end of the vapor reservoir comprises using at least one member of a group consisting of o-ring seal, screw fitting, and crimping.

20. A method for sealing a vapor reservoir to an integrated waveguide chip, the method comprising:
   cleaving the chip to a desired size;
   attaching a first end of the vapor reservoir over a first open end of a hollow waveguide comprised in the chip, wherein the vapor reservoir comprises a metallic cylinder, and wherein epoxy is used to form an air-tight seal between the first end of the vapor reservoir and the chip;
   placing the chip and the vapor reservoir in a controlled environment glovebox filled with nitrogen;
   introducing alkali metal droplets into the vapor reservoir; and
   sealing a second end of the vapor reservoir by crimping.

* * * * *